United States Patent
Paul et al.

(10) Patent No.: US 7,364,647 B2
(45) Date of Patent: Apr. 29, 2008

(54) LAMINATED FLOW DEVICE

(75) Inventors: Phillip H. Paul, Livermore, CA (US); David W. Neyer, Castro Valley, CA (US); Jason E. Rehm, Alameda, CA (US)

(73) Assignee: Eksigent Technologies LLC, Dublin, CA (US)

( * ) Notice: Subject to any disclaimer, the term of this patent is extended or adjusted under 35 U.S.C. 154(b) by 315 days.

(21) Appl. No.: 10/198,223

(22) Filed: Jul. 17, 2002

(65) Prior Publication Data

US 2004/0011648 A1   Jan. 22, 2004

(51) Int. Cl.
 *B67D 5/00* (2006.01)
 *G05D 7/06* (2006.01)

(52) U.S. Cl. ............... 204/600; 156/223; 422/100
(58) Field of Classification Search ........... 204/600, 204/450; 137/833; 422/100; 156/223
See application file for complete search history.

(56) References Cited

U.S. PATENT DOCUMENTS

| | | | |
|---|---|---|---|
| 4,240,889 A * | 12/1980 | Yoda et al. | 204/403.09 |
| 4,999,069 A | 3/1991 | Brackett et al. | |
| 5,037,457 A | 8/1991 | Goldsmith et al. | |
| 5,041,181 A | 8/1991 | Brackett et al. | |
| 5,126,022 A | 6/1992 | Soane et al. | |
| 5,534,328 A | 7/1996 | Ashmead et al. | |
| 5,628,890 A * | 5/1997 | Carter et al. | 204/403.05 |
| 5,888,390 A | 3/1999 | Craig | |
| 5,958,203 A | 9/1999 | Parce et al. | |
| RE36,350 E | 10/1999 | Swedberg | |
| 5,989,402 A * | 11/1999 | Chow et al. | 204/601 |
| 5,997,708 A | 12/1999 | Craig | |
| 6,007,690 A | 12/1999 | Nelson et al. | |
| 6,013,164 A | 1/2000 | Paul et al. | |
| 6,019,882 A | 2/2000 | Paul et al. | |
| 6,054,034 A | 4/2000 | Soane et al. | |
| 6,074,725 A | 6/2000 | Kennedy | |
| 6,080,295 A | 6/2000 | Parce et al. | |
| 6,100,107 A | 8/2000 | Lei et al. | |
| 6,113,766 A * | 9/2000 | Steiner et al. | 204/606 |
| 6,126,723 A | 10/2000 | Drost et al. | |
| 6,129,973 A | 10/2000 | Martin et al. | |
| 6,150,089 A * | 11/2000 | Schwartz | 435/6 |
| 6,156,273 A | 12/2000 | Regnier et al. | |
| 6,176,962 B1 | 1/2001 | Soane et al. | |

(Continued)

FOREIGN PATENT DOCUMENTS

EP   0421234   10/1991

(Continued)

OTHER PUBLICATIONS

J. Haisma, "*Direct Bonding in Patent Literature*", Philips. J. Res. 49, pp. 165-170 (1995).

(Continued)

*Primary Examiner*—Kaj K. Olsen
(74) *Attorney, Agent, or Firm*—Jeffrey G. Sheldon; Sheldon Mak Rose & Anderson

(57) ABSTRACT

A laminated flow device comprises a porous material encapsulated within bonding material. The porous material forms a flow path and the bonding material forms an enclosure surrounding the flow path. Micro-components, such as capillaries, electrodes, reservoirs, bridges, electrokinetic elements, and detectors, can be encapsulated within the device.

9 Claims, 8 Drawing Sheets

U.S. PATENT DOCUMENTS

| | | | |
|---|---|---|---|
| 6,210,986 B1 | 4/2001 | Arnold et al. | |
| 6,267,858 B1 | 7/2001 | Parce et al. | |
| 6,287,438 B1 * | 9/2001 | Knoll | 204/409 |
| 6,287,440 B1 * | 9/2001 | Arnold et al. | 204/450 |
| 6,352,577 B1 | 3/2002 | Martin et al. | |
| 6,418,968 B1 | 7/2002 | Pezzuto et al. | |
| 6,719,535 B2 | 4/2004 | Rakestraw et al. | 417/50 |
| 6,729,352 B2 | 5/2004 | O'Connor et al. | |
| 6,755,211 B1 | 6/2004 | O'Connor et al. | |
| 6,770,182 B1 | 8/2004 | Griffiths et al. | 204/453 |
| 6,814,859 B2 | 11/2004 | Koehler et al. | 210/198.2 |
| 2002/0048425 A1 | 4/2002 | McBride et al. | |
| 2002/0056639 A1 | 5/2002 | Lackritz et al. | |
| 2002/0059869 A1 | 5/2002 | Martin et al. | |
| 2002/0066639 A1 | 6/2002 | Taylor et al. | |
| 2002/0125134 A1 | 9/2002 | Santiago et al. | 204/450 |
| 2002/0166592 A1 | 11/2002 | Liu et al. | 137/825 |
| 2002/0185184 A1 | 12/2002 | O'Connor et al. | |
| 2002/0187074 A1 | 12/2002 | O'Connor et al. | |
| 2002/0187557 A1 | 12/2002 | Hobbs et al. | |
| 2002/0189947 A1 | 12/2002 | Paul et al. | |
| 2002/0195344 A1 | 12/2002 | Neyer et al. | |
| 2003/0052007 A1 | 3/2003 | Paul et al. | |
| 2003/0061687 A1 | 4/2003 | Hansen et al. | 23/295 |
| 2003/0116738 A1 | 6/2003 | O'Connor et al. | |
| 2003/0143081 A1 | 7/2003 | Rakestraw et al. | 417/48 |
| 2003/0150792 A1 | 8/2003 | Koehler et al. | 210/321 |
| 2003/0198130 A1 | 10/2003 | Karp et al. | |
| 2003/0198576 A1 | 10/2003 | Coyne et al. | |
| 2003/0206806 A1 | 11/2003 | Paul et al. | |
| 2003/0226754 A1 | 12/2003 | Le Febre | 204/451 |
| 2004/0011648 A1 | 1/2004 | Paul et al. | |
| 2004/0074784 A1 | 4/2004 | Anex et al. | 205/674 |
| 2004/0087033 A1 | 5/2004 | Schembri | 436/180 |
| 2004/0101421 A1 | 5/2004 | Kenny et al. | 714/313 |
| 2004/0115731 A1 | 6/2004 | Hansen et al. | 435/7.1 |
| 2004/0118189 A1 | 6/2004 | Karp et al. | |
| 2004/0129568 A1 | 7/2004 | Seul et al. | 204/450 |
| 2004/0163957 A1 | 8/2004 | Neyer et al. | 204/450 |
| 2004/0182709 A1 | 9/2004 | Griffiths et al. | 204/601 |
| 2004/0238052 A1 | 12/2004 | Karp et al. | |
| 2004/0241004 A1 | 12/2004 | Goodson et al. | 417/48 |
| 2004/0241006 A1 | 12/2004 | Taboryski et al. | 417/49 |
| 2004/0247450 A1 | 12/2004 | Kutchinski et al. | 417/48 |

FOREIGN PATENT DOCUMENTS

| | | |
|---|---|---|
| EP | 1063204 | 12/2000 |
| JP | 03-087659 | 4/1991 |
| WO | WO 99/16162 | 4/1999 |
| WO | WO 2004/027535 | 4/1999 |
| WO | WO 00/55502 | 9/2000 |
| WO | WO 01/25138 | 4/2001 |
| WO | WO 02/086332 | 10/2002 |

OTHER PUBLICATIONS

M.A. Roberts, J.S. Rossier. P. Bercier and J. Girault, "*UV Laser Machined Polymer Substrates for the Development of Microdiagnostic Systems,*" Anal. Chem. 69, pp. 2035-2042 (1997).

P.M. Martin, D.W. Matson, W.D. Bennett, Y.Lin and D.J. Hammerstrom, "*Laminated Plastic Microfluidic Components for Biological and Chemical Systems,*" J. Vac. Sci. Technol. A 17, pp. 2264-2269 (1999).

V.K. Stokes, "*Joining Methods for Plastics and Plastic Composites: An Overview.*" Poly. Eng. and Sci. 29 pp. 1310-1324 (1989).

N.M. Watson and M.G. Murch, "*Recent Developments in Hot Plate Welding of Thermoplastics,*" Poly. Eng. and Sci. 29 pp. 1382-1386 (1989).

T. Jimbo, M. Higa, N. Minoura and A. Tanioka, "*Surface Characterization of Poly(acrylonitrite) Membranes: Graft-Polymerized with Ionic Monomers as Revealed by Zeta Potential Measurements,*" Macromolecules 31 pp. 1277-1284 (1998).

F. Klein. "*Affinity Membranes: a 10 Year Review,*" J. Membrane Sci. 179 pp. 1-27 (2000).

K. Takata, Y. Yammamoto and T. Sata, "*Modification of Transport Properties of Ion Exchange Membranes,*" J. Membrance. Sci. 179 pp. 101-107 (2000).

S. Belfer, Y. Purinson, R. Fainshtein, Y. Radchenko and O. Kedem, "*Surface Modification of Commercial Polyamide Reverse Osmosis Membranes,*" J. Membrane Sci. 139 pp. 175-181 (1998).

A. Mroz, M. Borchardt, C. Diekmann, K. Cammann, M. Knoll, and C. Dumschat. "*Disposable Reference Electrode,*" Analyst 123 pp. 1373-1376 (1998).

PCT Search Report dated Mar. 25, 2004.

Jack R. Vinson, *Adhesive Bonding of Polymer Composites*, Polymer Engineering and Science, Mid-Oct. 1989, vol. 29, No. 19, pp. 1325-1331.

Holger Becker; Claudia Gartner, *Polymer microfabrication methods for microfluidic analytical applications*, Electrophoresis 2000, 21, 12-26.

M. Gongora-Rubio, et al. *The utilization of low temperature co-fired ceramics (LTCC-ML) technology for meso-scale EMS, a simple thermistor based flow sensor*, Sensors and Actuators 73 (1999) 215-221.

US 6,406,905, 06/2002, Parce et al. (withdrawn)

* cited by examiner

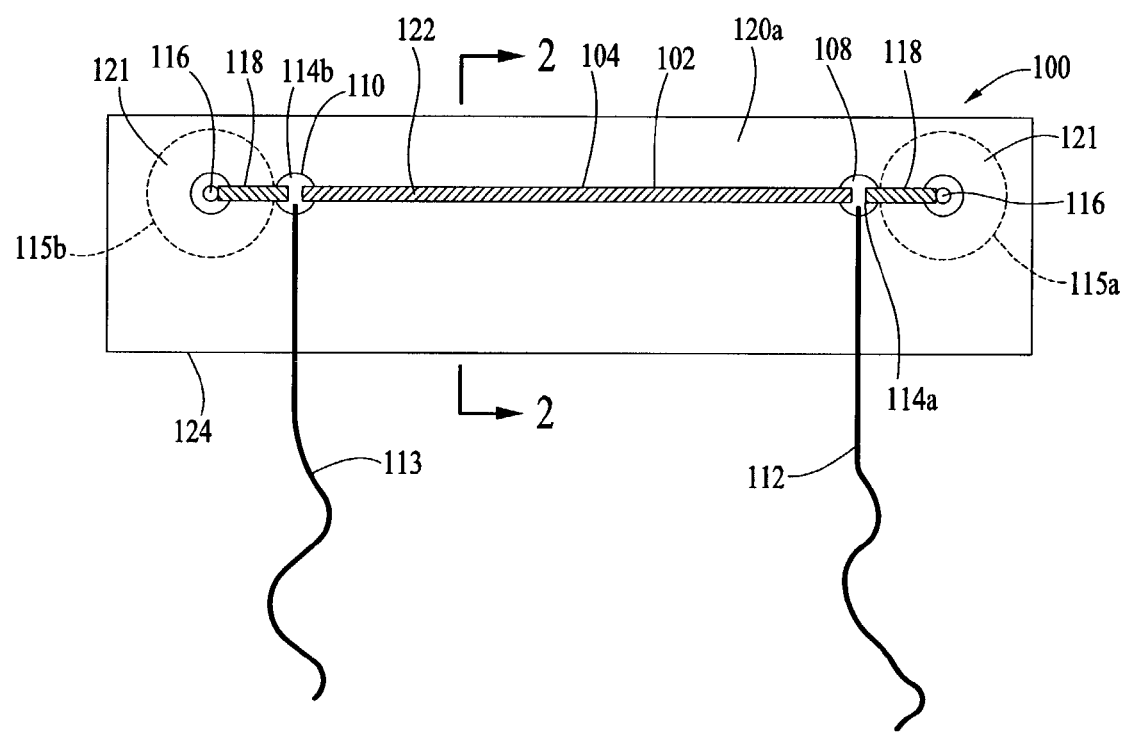
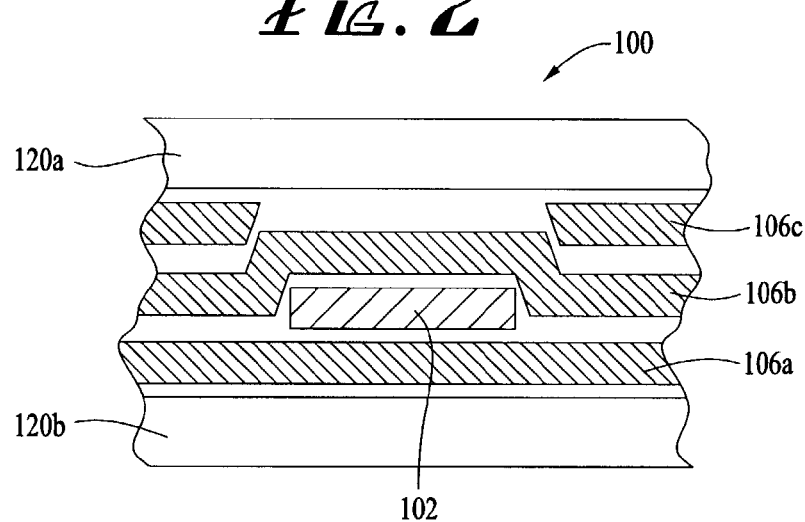

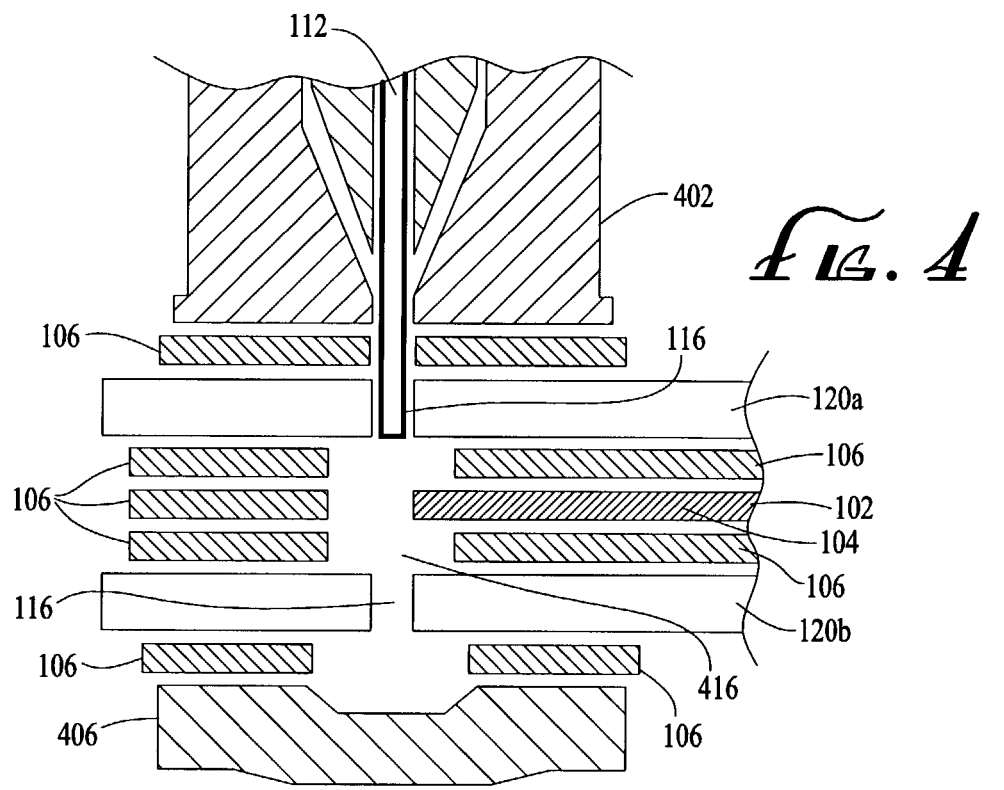
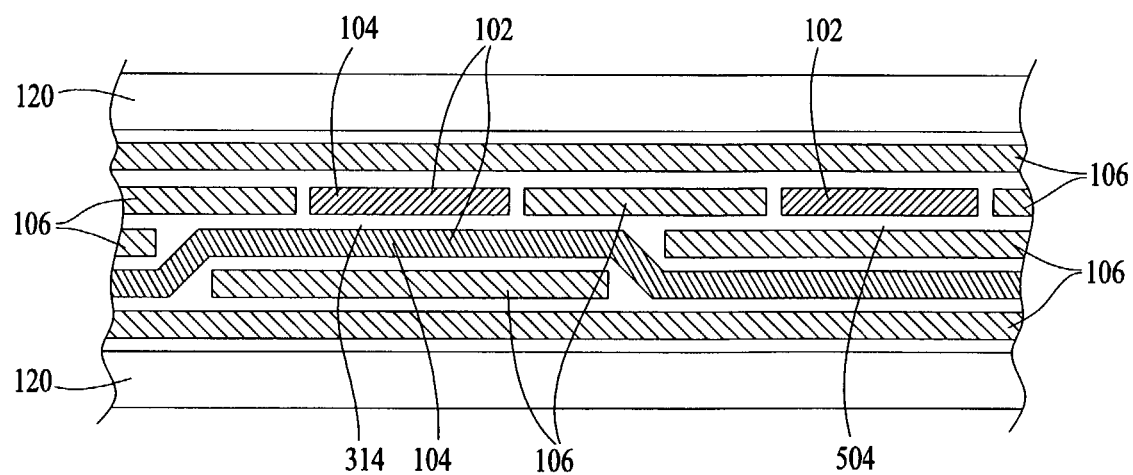

LAMINATED FLOW DEVICE

BACKGROUND

Microfluidic devices are becoming an important component of instrumentation in many areas of technology including, for example, chemical synthesis and analysis. Conventionally, channels for fluid flow in microfluidic devices are machined, etched, or molded into a planar substrate. The channels are then enclosed by attaching a second substrate. These channels can be filled with various liquids used for chemical processing or with a gel used for electrophoric separations, for example.

In order to perform more general chromatography in this same device, it is necessary to incorporate a stationary phase within the channels. This can be done by directly etching chromatographic supports into the channels. However, it is not possible with current technology to easily etch supports with cross sections large enough and pore sizes small enough for high performance liquid chromatography (HPLC). Further, the surface of the supports must be derivatized after they are enclosed by the second substrate. Since the surface of the supports cannot be derivatized before enclosure, supports with different surface chemistries must be derivatized individually. This increases manufacturing costs and decreases production yield.

Alternatively, a stationary phase can be incorporated by packing open conduits with chromatographic porous particles, silica, for example, or a castable porous polymer. However, packing a channel with a single porous material is fairly difficult and is thus subject to poor manufacturing yield. It is even more difficult to pack two different materials into a channel or channels that are in fluidic communication.

Methods of fabricating microfluidic structures in the prior art include: U.S. Pat. Nos. 6,074,725, 6,156,273 and 6,176,962. These methods suffer from the aforementioned disadvantages.

Accordingly, there is a need to easily and inexpensively incorporate surface derivatized porous materials having a pore size small enough for HPLC and for high-pressure electrokinetic devices into a single micro-flow device. There is also a need to incorporate more than one porous material into a single micro-flow device.

SUMMARY

The present invention is directed toward a flow device that satisfies this need. The flow device comprises a laminate having a porous material therein. The porous material forms a flow path and the laminate forms a non-permeable barrier surrounding the flow path. The flow path has a fluid inlet and a fluid outlet through the laminate.

The pores of the porous material can have a diameter of less than ten microns, which is small enough for HPLC, or less than one micron, which is appropriate for high pressure electrokinetic devices. The porous material can be derivatized prior to lamination. The porous material can be a porous membrane film. More than one porous material can be within the laminate. The laminate can also include a means for forcing a fluid from the inlet through the flow path to the outlet, such as means for generating an electroosmotic flow or a pressure differential. The laminate can also contain a detector, such as an optical fiber. The flow path can withstand pressures in excess of 500 psi. A substrate can support the laminate.

BRIEF DESCRIPTION OF THE DRAWINGS

These and other features, aspects and advantages of the present invention will become better understood with regard to the following description, appended claims, and accompanying drawings where:

FIG. 1 is a plan view of a laminated flow device embodying the present invention.

FIG. 2 is an exploded, partially cut-away, cross-section view of the device of FIG. 1 at line 2-2 in FIG. 1.

FIG. 4 is an exploded, partially cut away, cross-section view of a laminated flow device embodying the present invention and illustrating attachments for an HPLC fitting and a pressure transducer.

FIG. 5 is an exploded, partially cut away, cross-section view of another laminated flow device embodying the invention.

DESCRIPTION

Figure 3A:
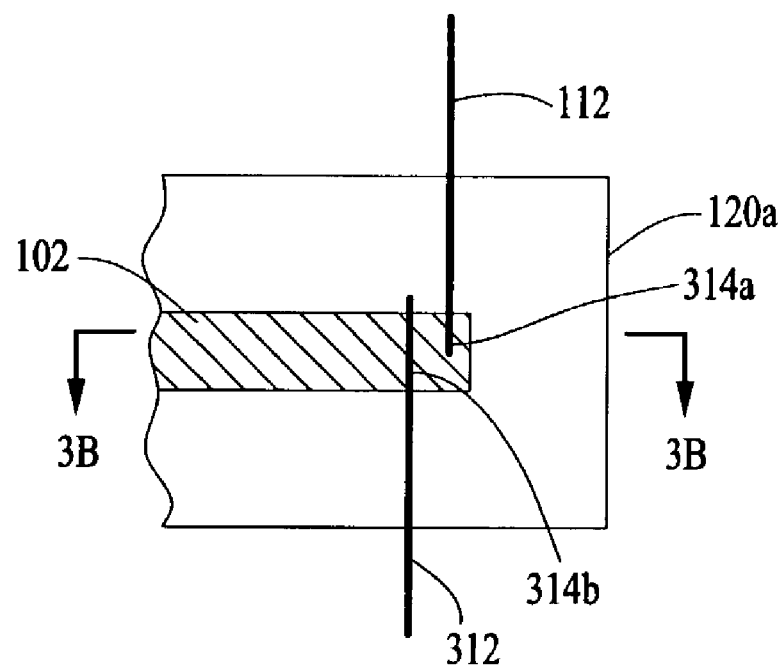
FIG. 3A is a top plan view of a junction that can be used in an embodiment of the invention.

The present invention is directed to a flow device that includes a porous material that is encapsulated within a bonding material, also referred to herein as a laminating material or lamination material, that forms a channel enclosure. In other words, the porous material is laminated.

With references to the drawings, and particularly FIGS. 1 and 2, a device 100 includes a porous material 102 that forms a flow path 104 and a bonding material 106 forms a non-permeable barrier surrounding the flow path. The flow path 104 is along a longitudinal axis of the porous material 102 and has a fluid inlet 108 and a fluid outlet 110. An upper substrate 120a and a lower substrate 120b sandwich the bonding material 106 and provide structural support.

A fluid 122 can flow in this device from a first pigtailed capillary 112, i.e., a capillary having one end that is laminated to a device and the opposite end attached to another device, through a first junction 114*a*, through a section of a strip of the porous material 102, through a second junction 114*b* and out of a second pigtailed capillary 113. Electrical current flow is from an electrode (not shown) located in a liquid-filled reservoir 115*a* though a reservoir liquid 121 which flows through a via 116 drilled in the upper substrate 120*a*. The current carried by the reservoir liquid 121 then passes through a porous media bridge 118 to the fluid 122 in the strip of porous material 102, and then through a like set of connections to an electrode (not shown) in a reservoir 115*b* at the other end. The reservoir liquid 121 serves to carry current and little or no reservoir liquid flows through the porous media 102.

This device 100 can serve as an electroosmotic (also known as electrokinetic) flow device which can be used for electrokinetic pumping or as part of a combined electroosmotic and pressure driven flow system, such as those disclosed in U.S. patent application Ser. No. 10/155,474 filed on May 24, 2002, and entitled Combined Electroosmotic and Pressure Driven Flow System, published as US 2002/0195344, and is incorporated herein by reference. Alternatively, a pressure differential or any other means shown in the art, such as a vacuum and a pump, can cause fluid to flow from the inlet to the outlet. The pressure differential can be created by any means known in the art.

All of the micro-components (not including the substrates 120*a* and 120*b*) are encapsulated within bonding material 106 that forms a laminate 124 except for the ends of the capillaries 112 and 113 as shown. The laminate 124 can form a "chip"—like device that may be integrated into a larger micro-fluidic system. Various types of porous and non-porous media can be laminated in one device. The device can form a planar flow system that can be multi-level.

As can be seen in FIG. 2, in one embodiment three layers of bonding material 106 are employed: a lower layer 106*a*, a middle layer 106*b*, and an upper layer 106*c*. The lower layer 106*a* and the middle layer 106*b* of bonding material encapsulate the porous material 102. The displacement of the middle layer 106*b* of bonding material by the presence of the porous material 102 is taken up with the upper 'gap-filling' layer 106*c* of bonding material. These layers 106*a*, 106*b* and 106*c* of bonding material are sandwiched between a rigid upper substrate 120*a* and a lower substrate 120*b* for mechanical support. In some embodiments, no substrates are used or the layers 106*a*, 106*b*, and 106*c* can be potted in any material commonly known in the arts for providing increased mechanical strength, desired thermal conductivity, or dielectric strength, herein referred to as a "potting material." Examples of such potting materials include, but are limited to, thermoset resin, epoxy, reinforced epoxy, castable acrylic, and silicone.

Figure 3B:
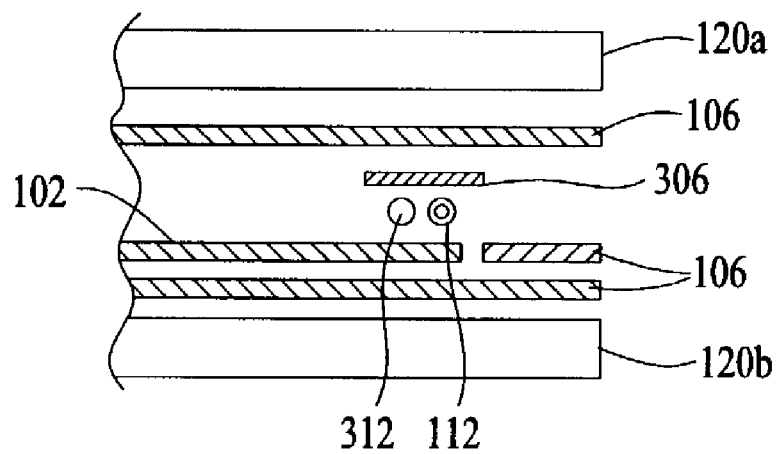
FIG. 3B is an exploded, cross-section view of the junction of FIG. 3A at line 3B-3B in FIG. 3A.

Fluid input/output connections to the porous materials 102 such as the junctions 114*a* and 114*b* shown in FIG. 1 can be made by any means known in the art or by a capillary pigtail connection 314*a* that is directly integrated and sealed in the bonding material 106 as illustrated in FIGS. 3A and 3B. A nonporous membrane 306 that substantially maintains its shape at the bond temperature and pressure, such as polypropylene, overlays the connection 314*a* between the porous material 102 and the first capillary 112. This type connection 314*a* is a "lap joint". The connection 314*b* between an electrode 312 and the porous material 102 is also a lap joint. The nonporous membrane 306 prevents plugging of the capillary 112 or complete encapsulation of the electrode 312 by the bonding material 106. Alternatively, one or more pieces of nonporous membrane 306 can cover a butt junction between two porous elements or a porous element and a capillary or electrode, for example. Preferably, the connection 114*a* can withstand, i.e., will not break under, high pressures, such as pressures equal to or greater than 500 psi, and has a low dead volume.

Other high pressure and low dead volume fluid input/output connections can be made by direct bonding. For example, connections can also be made by conventional HPLC fittings 402, illustrated in FIG. 4, that are bonded by bonding material 106 to the upper substrate 120*a* and that communicate with the flow path 104 through a via 116 machined through the upper substrate. Vias may be through the upper substrate 120*a* and/or the lower substrate 120*b* and may be used to attach sensors, reservoirs, and electrodes or to provide a fluid connection, for example.

In the embodiment illustrated in FIG. 4, a small well 416 in the bonding material 106 is cut- or punched-out at the via 116 in the upper substrate 120*a* and the capillary 112 is extended into this well to provide a connection that is not sealed by the bonding material. A via 116 is also machined through the bottom substrate 120*b* and a pressure transducer 406 is bonded to the lower substrate 120*b* across the via, illustrating another example of a high pressure and low dead volume connection.

Connections made by direct bonding can withstand high pressures. For example: A standard PEEK (polyetheretherketone) or stainless steel HPLC fitting has an internal wetted diameter of less than 1 mm diameter and a 5 to 10 mm diameter flange that can be bonded to the upper or lower substrate 120*a* or 120*b*. Such a fitting, bonded with a film having 900-psi tensile strength, a value typical of many polymer bonding materials, provides the mechanical strength required for operation at pressures of over 10,000 psi, which generally exceeds the pressure rating of common HPLC fittings.

FIG. 5 shows an implementation of a lap joint connection 314 between different strips of porous material 102, one strip being perpendicular to the page. The strips do not have to be comprised of the same type of porous material but can be comprised of porous material having different characteristics. Fluid and electrical connection is made by the physical overlap hence direct contact of the porous media 102 forming the two intersecting flow paths 104. Five layers of bonding material 106 are employed to encapsulate the porous materials 102.

FIG. 5 also illustrates an avoided lap-joint interconnect 504. In conventional trench-and-cover chips, the flow circuit is essentially in one plane, and thus the only means of avoiding a channel intersection is to stack up more etched substrates interconnected with vias. FIG. 5 is an example of how the present invention can be directly and simply extended to multilayer flow structures.

Figure 6A:
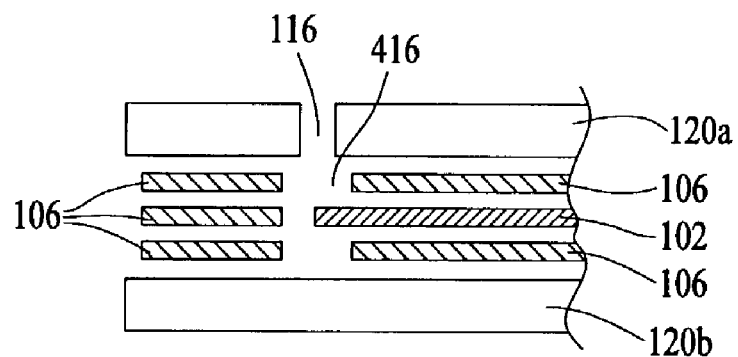
FIG. 6A is an exploded, partially cut-away, cross-section view of yet another laminated flow device embodying the invention and illustrating a first junction between a via and a porous material.
Figure 6B:
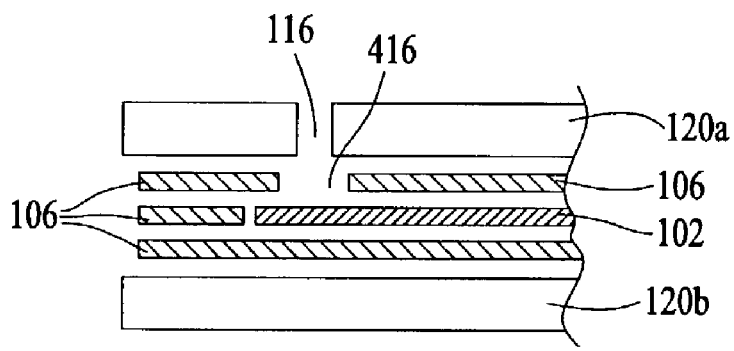
FIG. 6B is an exploded, partially cut away, cross-section view of the laminated flow device of FIG. 6A illustrating a second junction between a via and a porous material.
Figure 6C:
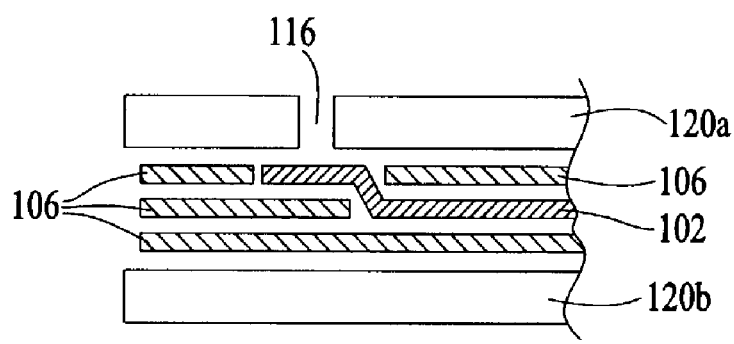
FIG. 6C is an exploded, partially cut away, cross-section view of the laminated flow device of FIG. 6A and illustrating a third different junction between a via and a porous material.
Figure 7A:
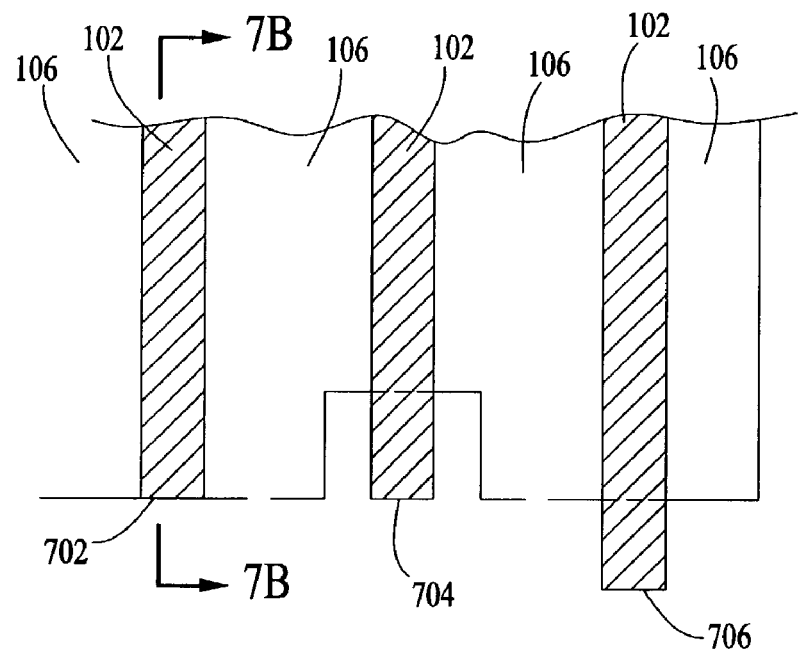
FIG. 7A is a partially cut-away, top plan view of a laminated flow device embodying the invention and illustrating a porous material edge connection.
Figure 7B:
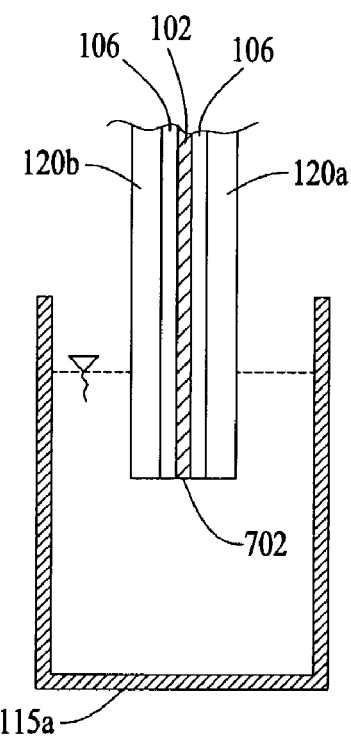
FIG. 7B is a partially cut-away, cross section view of the laminated flow device of FIG. 7A at line 7B-7B of FIG. 7A.

Low pressure fluid input/output connections to the porous materials can be made by any of the high pressure connections described or any other connection known in the art or by direct contact of the porous material 102 with the fluid that enters the flow device through a via 116 as illustrated in FIGS. 6A-6C or by placing exposed porous materials in contact with a fluid as illustrated in FIGS. 7A and 7B.

In FIG. 6A the porous material 102 is directly exposed to fluid in well 416 that is open from the upper substrate 120*a* to the lower substrate 120*b*. The porous material 102 in FIG. 6B is exposed to fluid in a well 416 that is open to only the upper substrate 120*b*. In FIG. 6C the porous material 102 is folded to make a direct contact with the via 116.

Alternatively, a low pressure connection can be made with porous material 102 that has an edge 702 flush with the bonding material 106, forms a recessed wick 704, or forms a wick 706, as illustrated in FIG. 7A. The flush edge 702, recessed wick 704, or wick 706 of a porous material 102 can be placed in a fluid reservoir 115a for fluid input or output. FIG. 7B shows the flush edge 702 in the reservoir 115a. The reservoir 115a can contain an electrode with the porous material 102 forming part of an electroosmotic flow device or a bridge, such as the bridge 118 in FIG. 1 or a bridge as described in U.S. patent application Ser. No. 10/137,215, filed on May 1, 2002 and entitled Bridges, Elements and Junctions for Electroosmotic Flow Systems, now U.S. Pat. No. 7,060,170 incorporated herein by reference. Arrays of such edge connections can be used in conjunction with separate reservoirs or reservoirs in the form of a replaceable cartridge pack.

Figure 8:
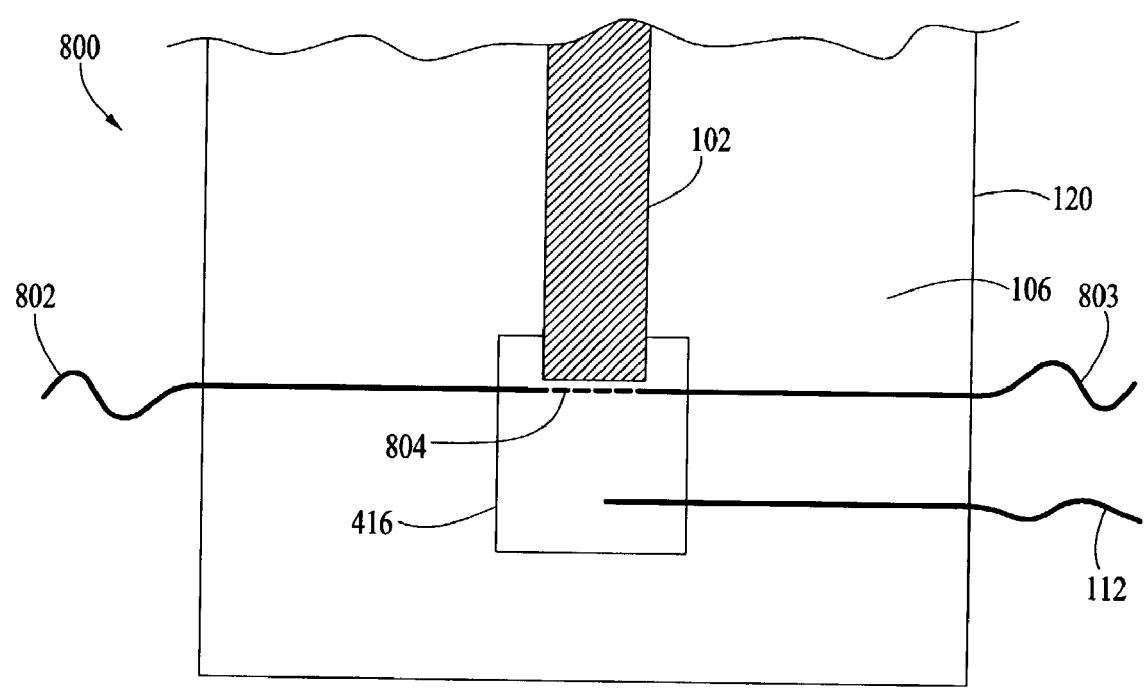
FIG. 8. is a partially cut-away, top plan view of a laminated flow device embodying the invention and illustrating an optical detector.

Optical connections can be made with optical fiber pigtails 802 that are directly integrated and sealed into the bonding material 106 layers as illustrated in FIG. 8. FIG. 8 shows an example optical detection absorption cell 800. The cell 800 is located at the outlet of a flow path formed by the porous material 102. Light from one fiber 802 transilluminates the fluid flowing out of the porous material 102 and into an absorption optical path 804. After passing through the absorption optical path 804, the fluid flows out of the device through pigtailed capillary 112. As the composition of the fluid or tracer components in the fluid varies, the amount of optical absorption may vary. A portion of the absorbed light is collected by a second optical fiber 803 and thence to an optical detector (not shown). A third optical fiber (not shown) may be included and positioned at an angle to the absorption optical path 804 to collect any induced fluorescence or otherwise scattered light. The third optical fiber can be substantially in the plane of or normal to the plane of the flow device when the flow device is substantially planar. The optical fibers 802 and 803 can be prealigned under illumination and thermally or adhesively tacked into place prior to bonding. In a similar fashion, metal or carbon fiber electrodes (or arrays of same) may be integrated into the bonding material 106 and positioned into the flowing liquid to act as elements of an electrochemical detection cell.

A wide variety of porous materials 102 can be used in conjunction with the invention. The porous material 102 used can be chosen for a suitable surface chemistry, surface charge, pore size, pore topology, and formation factor. Porous materials 102 include porous polymers, membranes, silica, alumina and nylon. Fine-pored material having a low surface charge density of about $10^{12}$ charges/cm$^2$ (as a reference, ionized silica is about $3.5 \; 10^{14}$ charges/cm$^2$), such as hydrophilic polyvinylidene fluoride, polyethersulfone, or polyvinylalcohol can be used as bridges. Fine-pored material having a high surface charge density (greater than about $5 \; 10^{14}$ charges/cm$^2$), such as Nafion® membranes can be used as ion-exchange elements. Hydrophobic porous materials 102 such as polypropylene or PTFE (polytetrafluoroethylene), also known as Teflon® membranes can be used as vents.

Porous materials 102 can be used as produced or can be derivatized to alter their surface chemistry. Any method known in the art can be used to modify or derivatize the surface chemistry of the porous materials 102 such as those disclosed in T. Jimbo, M. Higa, N. Minoura and A. Tanioka, 'Surface characterization of polyacrylonitrile membranes: Graft-polymerized with ionic monomers as revealed by zeta potential measurements,' Macromolecules 31 pp. 1277-1284 (1998). E. Klein, 'Affinity membranes: a 10 year review,' J. Membrane Sci. 179 pp. 1-27 (2000). K. Takata, Y. Yammamoto and T. Sata, 'Modification of transport properties of ion exchange membranes,' J. Membrane. Sci. 179 pp101-107 (2000). S. Belfer, Y. Purinson, R. Fainshtein, Y. Radchenko and O. Kedem, 'Surface modification of commercial polyamide reverse osmosis membranes,' J. Membrane Sci. 139 pp. 175-181 (1998), which are incorporated herein by reference. The porous material 102 as-coated or as derivatized are preferably stable at least up to the bond temperature of the bonding material 106.

One advantage of the invention is the ability to modify the porous material 102 before incorporation into the device 100. This overcomes the extreme difficulty and low manufacturing yield of in situ derivatization generally required when using conventional trench-cover-fill methods of chip manufacture.

Preferably the porous material 102 is in the form of a membrane sheet or film which can be easily manufactured with good dimensional tolerance, has an appropriate thickness for bonding (approx. 100 microns), is easily handled and can be cut into strips or pieces of the appropriate size, and which facilitates derivatization before lamination. The pore geometry of the sheet is chosen with the design of the flow system in mind, specifically whether fluid flow will be normal to the plane of the sheet or in the plane of the sheet along its length, which is referred to herein as "longitudinal flow". Sheets of porous material membranes are generally intended for use with fluid flow directed normal to the plane of the material. However, many porous materials have an isotropic pore geometry and are thus suitable for flow in the plane of the membrane. Some ultra-filtration membranes are manufactured with a pore size distribution that is highly asymmetric in the direction normal to the plane of the membrane. Such materials are not suitable for applications requiring uniform longitudinal flow. However, such materials can be successfully employed in a layered planar structure for integrated filtration or dialysis where a component of the flow is normal to the original plane of the membrane.

Some porous membrane materials have a longitudinally anisotropic pore structure, i.e., the pore structure facilitates longitudinal flow in a preferred direction. Such materials are suitable for usage where longitudinal flow is desired and the anisotropy is reproducible in manufacturing. Preferably, when this type of material is used, it is oriented to take advantage of the different flow properties presented by the anisotropy.

The porous material 102 can be cut into strips or any shape using any method known in the arts of printing and paper handling, including kiss- or die-cutting. For example, for chromatographic separation, the porous material 102 can be a membrane cut into strips approximately 0.2 to 2 mm wide and as long as required by the application. These strips need not be straight but can be cut in a curved or serpentine fashion to provide a smaller footprint. Wider strips can be used, for example, to perform two-dimensional separations or to achieve high volumetric flow for preparative chromatography.

The porous material 102 used for chromatography can be selected according to principles well-known in the art. For example, the porous material 102 can have a pore size of less than ten microns, which is small enough for HPLC. The porous material 102 can be modified to provide a wide range of binding characteristics desirable in chromatographic separation, preconcentration, extraction, and electrophoresis. The modification can take place before the porous material is integrated into a flow device.

The porous material 102 can be specifically designed or modified to provide a wide range of characteristics desirable for fluid control and fluid pumping. For example, some fluid control can be achieved through selection of flow resistances of the porous material 102. The wide range of available pore diameters and formation factors can be used to provide a wide range of flow resistances. Microchannels composed of porous material 102 preferably are used for general fluid transport in the invention. Using a porous material 102 for fluid transport lessens hydrostatic siphoning due to different reservoir head heights and physical orientation.

Further, the porous material 102 can be selected to have a surface charge so that when an electric potential is applied to a fluid in the porous material 102, the fluid is pumped as in the flow system illustrated in FIG. 1. The porous material 102 can have a pore size of less than one micron, which is small enough for high-pressure electrokinetic devices. Materials having a native surface charge may be used, such as nylon or nitrocellulose. Alternatively, these and many other polymers can be derivatized to enhance, alter or add surface charge.

Common porous and bonding materials 102 and 106, respectively are approximately 50 to 250 microns thick. However, thicker and thinner materials can be used. The thicker the porous material 102, the higher the volumetric flow. Volumetric flow can also be increased by stacking layers of the porous material 102. When the porous material 102 is stacked, it can be interlayered with the bonding material 106.

Potential bonding materials 106 include, but are not limited to, homopolymers and copolymers of polyethylene and polypropylene, vinyl and acrylic acetates, polyesters, polyolefins, polyamids, polyimides, nitrites and nitrile-phenolics, chloro-fluoro-polymers, and thermally activated epoxies. These materials are commercially available as films with bond temperatures ranging from about 80° C. to 350° C.

Bonding materials 106 with various bond temperatures may be used in combinations. Lower temperature versions are preferred for bonding the micro-components. The high temperature versions are preferred for preparative bonding of subassemblies that will thus be unaffected by integration during a subsequent lower temperature bonding step.

Bonding materials 106 are generally selected for: bond temperatures consistent with preserving the physical and chemical integrity of the porous and other micro-component materials; chemical inertness; mechanical strength, particularly resistance to plastic deformation under pressure at normal operating temperatures; adhesion to porous materials and any other micro-components and substrates employed; and minimal shrinkage during bonding. Further, the bonding material preferably is pliable so that it conforms to the edge of the porous materials 102 and any other micro-components.

The thickness of the porous material 102 or micro-components and any associated gap-filling bond layers 106 preferably are near equal. Gap-filling bonding material 106 can be added or removed to compensate for the thickness of the porous material 102 or other micro-components. Some bonding material 106 in the gap-filling layer preferably is cut out to accommodate porous material 102 or other micro-components that are much thicker than the bonding material, so that the finished device is substantially planar. For thin elements, such as capillaries, wires, or optical fibers, where the diameter of the micro-component is approximately equal to the thickness of the bonding material 106, it is not necessary to cut the bonding material in the gap-filling layer.

The materials used for the substrates 120a and 120b can include glass, ceramic, metal and polymer. The substrate material and thickness are selected for: the ability to form a strong adhesive or cohesive bond with the bonding material 106; chemical compatibility with fluids used in the flow system; the mechanical strength needed to contain any fluid pressure in the flow system; the capacity to provide vias for fluid flow that are as fine as desired; the ability to mold, emboss, or machine as desired.

The substrate material can be pre-treated or coated with a primer to promote adhesion to the bonding material 106. For example, an untreated glass substrate will adhere poorly to many polymer bonding materials and is preferably pre-treated when used with polymer bonding materials. A glass substrate can be pretreated with a primer containing an amino-silane dissolved in methanol, for example. Generally, the substrate surface is first cleaned and dried, a coating of primer is applied, the coating is air- or oven-dried or cured, then the substrate can be stacked and laminated with porous materials 102 and other micro-components. The primer can be applied by any method known in the art such as: dip coating, painting and spin coating.

Several substrates, porous materials, and other micro-components can be laminated together in a stacked fashion in a single device. For example, open or packed capillary elements can be bonded into the device. Open capillaries can be used for point-to point connections within the device. Packed capillaries can be used to incorporate conventional particle-type chromatographic stationary phases. Electrode leads can be encapsulated within the bonding material 106 in order to provide electrical connections.

Typically, all the micro-components that are in a single device are stacked with bonding material 106 between the micro-components where no fluid flow is desired. The stack can then be compressed at a pressure of about 5-80 psi, for example and heated to the bond temperature specific to the bonding material 106 used. The bond pressure and temperature preferably are sufficiently high to promote a good bond as well as to cause the bonding material 106 to flow enough to fill in the gaps between micro-components but low enough to prevent significant intrusion of the bonding material into the pores of the porous material 102 and hence, prevent blockage of the flow path.

The device then cools. This process can be continuous or in batch. The process may employ any of the fixturing methods well known in the art, including: hot-shoe or thermode bonding, clamped static or conveyorized oven bonding, hydraulic or mechanical press bonding, hot-roller lamination bonding, or ultrasonic bonding or welding.

Bonding of components to the exterior of the substrates 120a and 120b can be made using thermoplastic bonding materials 106 and can be made in the same step as bonding the porous material 102, can be made in a preparative step using a higher bond temperature film, or can be made after the bonding of the porous material using a lower temperature bonding material, for example a thermally-activated epoxy film. Alternatively, components can be bonded using an adhesive or mechanical sealing method.

Advantages of a laminated flow device include: a wide variety of different micro-components can be easily incorporated into a device; fluid, optical and electrical input/output connections can be easily incorporated using pigtails rather than connectors; a high degree of pressure driven flow isolation can be achieved using a system that is filled with porous media (this results in more immunity from hydrostatic siphoning due to different reservoir head heights or physical orientation than a system using in whole or in part open channels); the ability to integrate a variety of types of micro-components in a planar and in a multilevel planar flow system device; can incorporate bulk-derivatized porous material; the bonding material forms a high integrity seal that can withstand pressures in excess of 500 psi; can have both a high rate fluid pump and a low flow rate fluid pump in one device; can be mass manufactured; can have an entire flow system in one device, for example, all the elements required for chromatographic separation and/or chemical processing, e.g., pump, injector, flow controller, separation elements, sample preparation, reactors, mixers, detection elements.

The laminated assemblies described herein can be used in conduction with conventional methods of making open-conduit chips. For example, open channels can be made by embossing or etching a substrate prior to bonding to the device. Alternatively, a laminated device can be subsequently laminated or otherwise connected to a conventional chip to form a hybrid system.

Figure 9A:
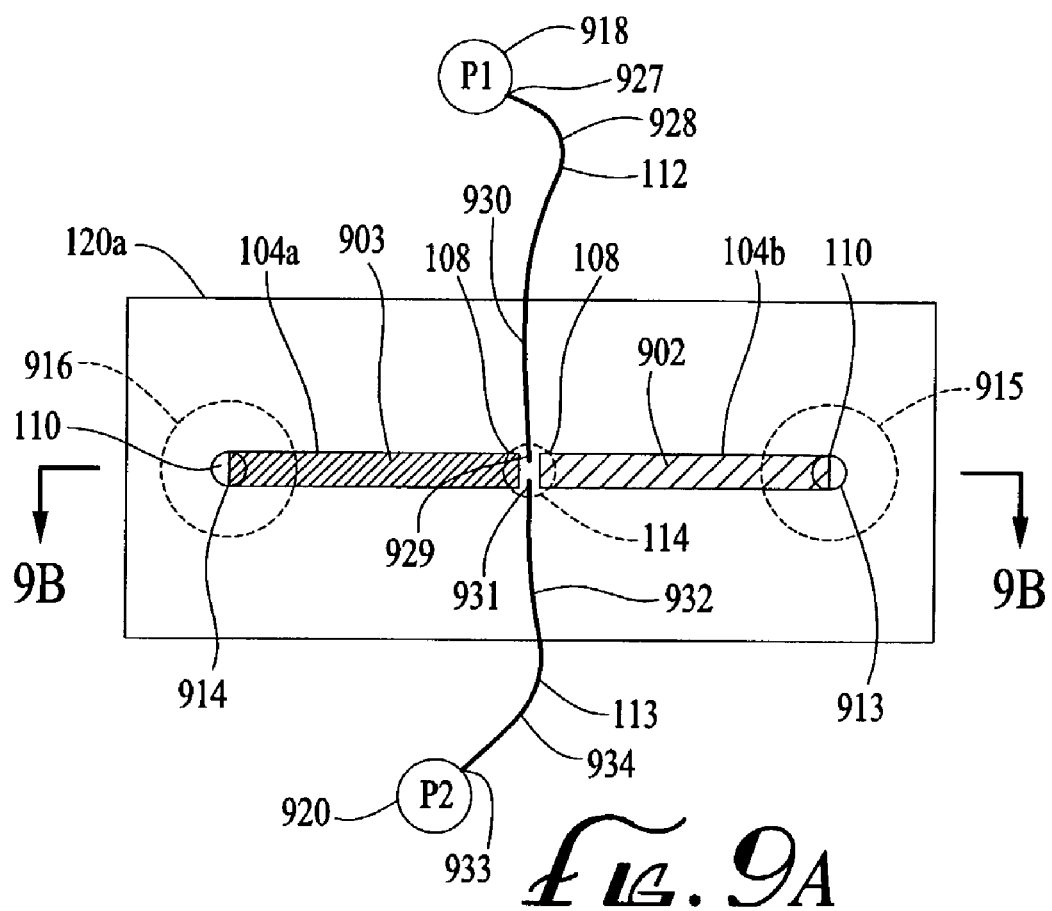
FIG. 9A is a top plan view of an embodiment of the present invention.
Figure 9B:
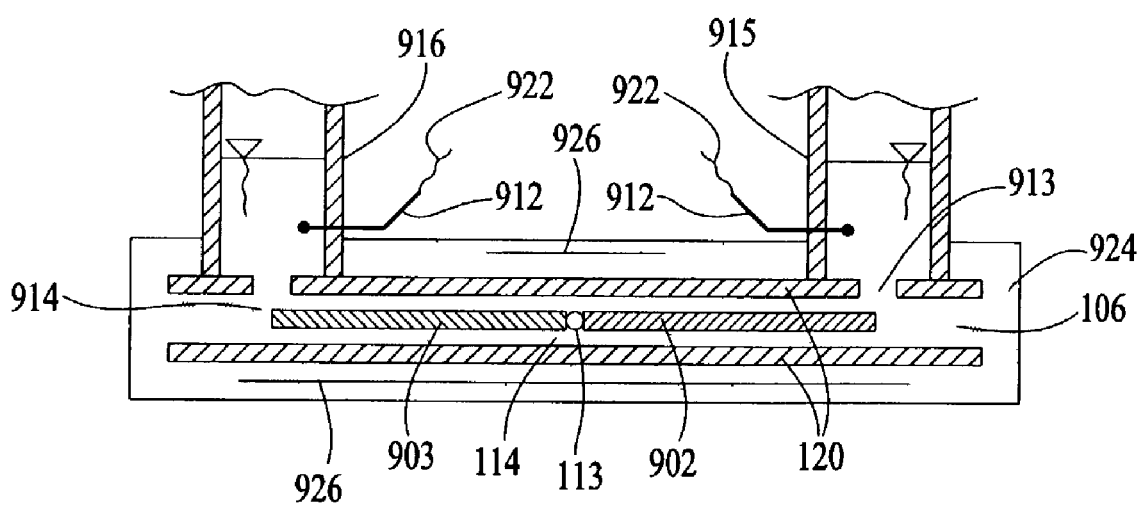
FIG. 9B is a cross section view of the embodiment illustrated in FIG. 9A at line 9B-9B in FIG. 9A.

Another example of a flow device containing multiple micro-components is illustrated in FIGS. 9A and 9B. The device is encapsulated in an epoxy 924 to provide further mechanical support and electrical isolation. Plates 926 provide additional mechanical support. The plates 926 can be comprised of any substantially rigid material.

Fluid flows from an inlet 927 at pressure $P_1$ 918 at an inlet end 928 of the first pigtailed capillary 112 through an outlet 929 at an outlet end 930 of the first pigtailed capillary to a first junction 114. A portion of the fluid flows from the first junction 114 through an inlet 931 in an inlet end 932 of the second pigtailed capillary 113 to an outlet 933 at pressure $P_2$ 920 at an outlet end 934 of the second pigtailed capillary 113, wherein $P_1$ preferably is greater than $P_2$. The outlet end 930 of the first capillary 112 and the inlet end 932 of the second capillary 133 are encapsulated by the bonding material 106. A portion of the fluid flows through the first junction 114, a positive zeta potential porous membrane 902 and a second junction 913 to a first reservoir 915. The positive zeta potential porous membrane 902 forms a flow path 104b within the laminate having a fluid inlet 108 and a fluid outlet 110. Another portion of the fluid flows through the first junction 114, a negative zeta potential porous membrane 903 and a third junction 914 to a second reservoir 916. The negative zeta potential porous membrane 903 also forms a flow path 104a within the laminate having a fluid inlet 108 and a fluid outlet 110.

The current path is from an electrode 912 in the second reservoir 916 through the fluid in the second reservoir 916, the fluid in the third junction 914, the fluid in the negative zeta potential porous membrane 903, the fluid in the first junction 114, the fluid in the positive zeta potential material 902, the fluid in the second junction 913, the fluid in the first reservoir 915 to an electrode 912 in the first reservoir 915. Leads 922 are used to attach the electrodes 912 to a power source (not shown). Because one porous membrane 902 has a positive zeta potential and the other porous membrane 902 has a negative zeta potential, fluid flows in opposite directions in the porous membranes and is drawn away from the capillaries 112 and 113 between the membranes when a potential is applied across the membranes. The flowrate of the portion of fluid that flows in the second capillary 113 and the flowrate of the portions that flow through the porous membranes 902 and 903 to the reservoirs 915 and 916 are determined by the size of the potential applied to the electrodes. A portion of fluid will still flow through the porous membranes 902 and 903 even if no potential is applied. This flow controller is described in U.S. patent application Ser. No. 10/155,474, filed on May 24, 2002, and entitled Combined Electroosmotic and Pressure Driven Flow System, published as US 2002/0195344, which is incorporated herein by reference.

Figure 10A:
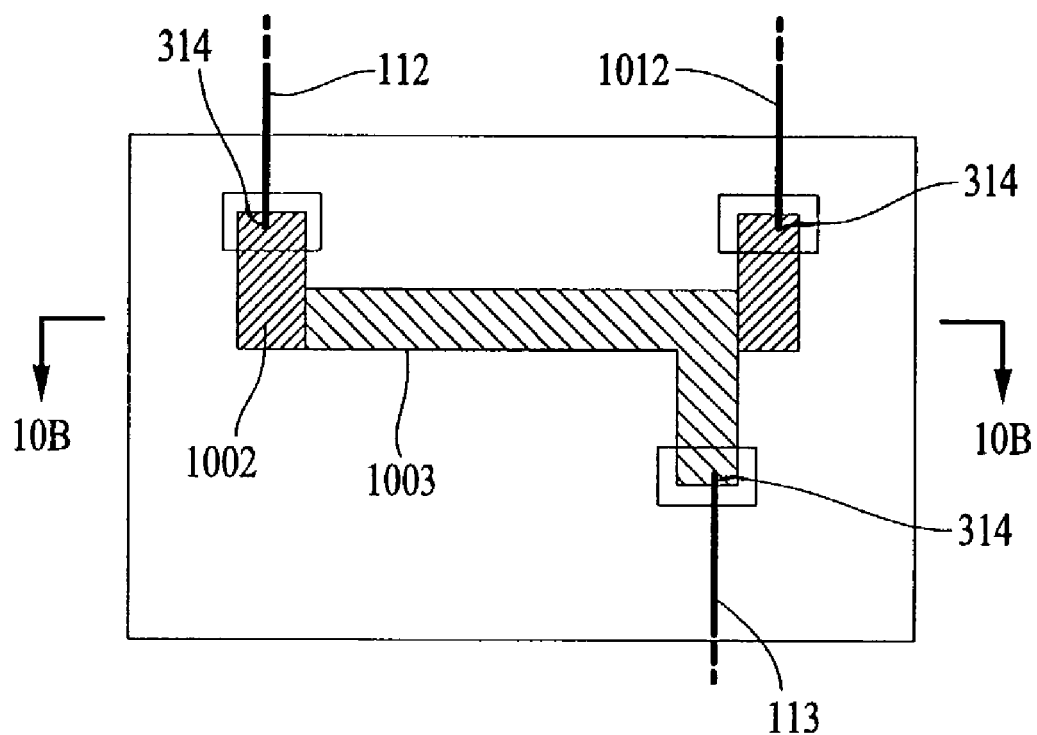
FIG. 10A is a top plan view of another embodiment of the present invention.
Figure 10B:
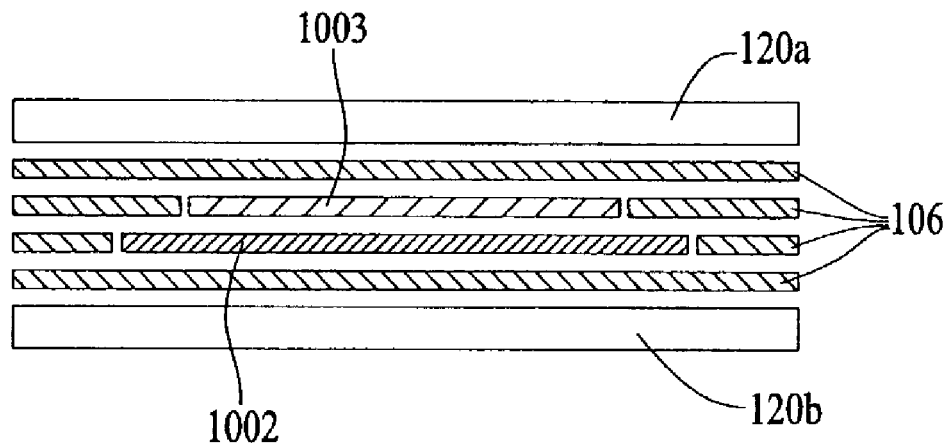
FIG. 10B is an exploded, cross section view of the embodiment illustrated in FIG. 10A at line 10B-10B.

An example of a flow device that can be used for filtration is illustrated in FIGS. 10A and 10B. A first sheet of porous material 1002 is stacked parallel to and in contact with a second sheet of porous material 1003. All fluids that are able to flow through the first sheet of porous material 1002 are not able to flow through the second sheet of porous material 1003. In other words, the first sheet of porous material 1002 has a greater permeability than the second sheet of porous material 1003. This can be accomplished, for example, by using a second sheet of porous material 1003 that has pores that are smaller in diameter than pores in the first sheet of porous material 1002. Hence, a fluid that contains some molecules that have a larger diameter than the pores of the second sheet of porous material 1003 but a smaller diameter than pores of the first sheet of porous material 1002 can flow through the first sheet of porous material completely, while the larger molecules of the fluid are prevented from flowing through the second sheet of porous material. The second sheet of porous material 1003 can have pores sufficiently small to exclude the larger molecules throughout the second sheet of porous material or can be asymmetric having small pores sizes along the portion of the sheet contacting the first sheet of porous material 1002.

Fluid, containing some molecules that are larger than the pores of the second sheet of porous material 1003 that are in contact with the first sheet of porous material 1002, enters the device from a first pigtailed capillary 112 then flows through a junction 314 into the first sheet of porous material. All of the fluid can flow longitudinally through the first sheet of porous material 1002. The portion of the fluid that contains molecules that are small enough to pass through the second sheet of porous material 1003 can flow laterally from the plane of the first sheet of porous material 1002 to the second sheet of porous material and out of the device through a second pigtailed capillary 113. The fluid that exits through the second pigtailed capillary 113 has been filtered so that it does not contain molecules too large to pass through the second porous material 1003. The rest of the fluid containing both large and small molecules exits from the device through a third pigtailed capillary 1012.

Although the present invention has been described in considerable detail with reference to certain preferred versions thereof, other versions are possible. For example, a flow device having features of the present invention can include a chromatographic column. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" for "step" clause as specified in 35 U.S.C. §112.

What is claimed is:

1. A flow device comprising:
   (a) a first porous membrane which forms a first flow path having a first liquid inlet and a first liquid outlet;
   (b) a second porous membrane which is in electrical communication with the first porous membrane and which forms a second flow path having a second liquid inlet and a second liquid outlet, the first and second porous membranes having different zeta potentials;
   (c) a non-permeable barrier comprising two layers of bonding material, wherein the two layers of bonding material (i) surround the first and second porous membranes, and (ii) are formed into a laminate by heating and compressing the layers of bonding material around the first and second porous membranes, so that the barrier conforms to the exterior of the first and the second porous membranes without blocking the first flow path or the second flow path;
   (d) a first capillary having an inlet end and an outlet end, the outlet end lying within the laminate and being in liquid communication with the first liquid inlet and the second liquid inlet, the inlet end of the first capillary having a pressure $P_1$;
   (e) a second capillary having an inlet end and an outlet end, the inlet end lying within the laminate and being in liquid communication with the outlet end of the first capillary, the outlet end of the second capillary having a pressure $P_2$, wherein $P_1 > P_2$; and
   (f) means for applying an electrical potential across the first and the second porous membranes;
   wherein when a liquid flows out from the outlet end of the first capillary, a first portion of the liquid flows in to the first liquid inlet, a second portion of the liquid flows in to the second liquid inlet, and a third portion of the liquid flows in to the inlet end of the second capillary.

2. A device according to claim 1 wherein the first portion has a first flow rate, the second portion has a second flowrate, and the third portion has a third flowrate and the first and second flowrates increase and the third flowrate decreases upon application of an electrical potential across the membranes.

3. A method of using the device of claim 1 comprising the steps of:
   (a) inserting fluid into the inlet end of the first capillary; and
   (b) applying an electrical potential to the electrodes.

4. A method for making a microfluidic device comprising the steps of:
   a. providing a first thermally conformable layer having a deformation temperature and a top surface;
   b. placing upon said top face a pre-formed porous element having an inlet end and an outlet end;
   c. defining first and second element interconnection regions within said first conformable layer, wherein said inlet and said outlet end of said porous element is located within said first and second element interconnection regions, respectively;
   d. placing an end of a first capillary within said first element interconnection region;
   e. placing an end of a second capillary within said second element interconnection region;
   f. placing the first and second shape maintaining non-permeable membranes over said first and second element interconnection regions, respectively, wherein each membrane has a thermal deformation temperature higher than said first thermally conformable layer's deformation temperature;
   g. placing a second thermally conformable layer upon said first thermally conformable layer, wherein said second thermally conformable layer covers and extends beyond said porous element, capillaries, and shape maintaining non-permeable membranes; and
   h. thermally bonding said first and second thermally conformable layers at a temperature at or above said deformation temperature of said first conformable layer and less than said first and second shape maintaining non-permeable membranes,
   wherein said first and second thermally conformable layers deform to conform and seal around said porous element and said capillaries but not within said first and second interconnection regions, thereby forming a first chamber within said first interconnection region, a second chamber within said second interconnection region, said first and second capillary ends being within said chambers, respectively, said first and second chambers each having surfaces formed from a portion of said first thermally conformable layer, a portion of said second thermally conformable layer and a portion of one of said first or second shape maintaining non-permeable membranes, respectively, thereby defining a fluid flow path from said first capillary end, through said porous element, and out said second capillary end.

5. The method of claim 4 further comprising the step of placing a plurality of porous elements having first and second ends, each end located within a separate one of a plurality of interconnection regions under said shape maintaining non-porous membranes prior to said bonding step.

6. The method of claim 5 further comprising the step of placing within three or more of said interconnection regions an end of one or more of a plurality of capillaries under said shape maintaining non-porous membranes prior to said bonding step.

7. The method of claim 4 further comprising the step of placing a portion of first and second electrodes in said first and second interconnection regions under said first and second shape maintaining non-porous membranes prior to said bonding step.

8. The method of claim 4 further comprising the step of placing a portion of at least one optical fiber within one of said interconnection regions under said shape maintaining non-porous membranes prior to said bonding step.

9. A laminated microfluidic device comprising:
   a. a first conformed layer;
   b. first and second interconnection regions;
   c. an end of a first capillary located within said first interconnection region;
   d. an end of a second capillary located within said second interconnection region;
   e. a porous element having first and second porous element ends, said first porous element end located within said first interconnection region and said second porous element end located within said second interconnection region;
   f. a first and second non-porous membranes, each covering one of said first and second interconnection regions;
   g. a second conformed layer bonded to said first conformed layer with said capillaries, porous element, and non-porous membranes encapsulated therebetween;
   h. first and second fluid chambers within said interconnection regions, each fluid chamber having therein a first surface formed from a portion of one of said first or second non-porous membranes, respectively, a second surface formed from a portion of said first conformed layer, and third surface formed from a portion of said second conformed layer, and, i. a contiguous fluid flow path formed between said first and second conformed layers, said fluid path extending from said first capillary end, through said first fluid chamber, through said porous element, through said second fluid chamber, and out said second capillary end.

* * * * *